US011041786B2

(12) United States Patent
Kosaka et al.

(10) Patent No.: US 11,041,786 B2
(45) Date of Patent: Jun. 22, 2021

(54) OIL EXTRACTION AGENT CONTAINING TRIMERIC OR HIGHER OLIGOMERS OF CHLOROTRIFLUOROETHYLENE

(71) Applicant: HORIBA Advanced Techno, Co., Ltd., Kyoto (JP)

(72) Inventors: Ryota Kosaka, Kyoto (JP); Katsunobu Ehara, Kyoto (JP)

(73) Assignee: HORIBA ADVANCED TECHNO, CO., LTD., Kyoto (JP)

( * ) Notice: Subject to any disclaimer, the term of this patent is extended or adjusted under 35 U.S.C. 154(b) by 0 days.

(21) Appl. No.: 16/450,571

(22) Filed: Jun. 24, 2019

(65) Prior Publication Data
US 2019/0391057 A1 Dec. 26, 2019

(30) Foreign Application Priority Data

Jun. 26, 2018 (JP) .............................. JP2018-121394

(51) Int. Cl.
C07C 19/10 (2006.01)
G01N 1/40 (2006.01)
G01N 33/28 (2006.01)
G01N 21/3577 (2014.01)
C07C 21/18 (2006.01)
C07C 17/281 (2006.01)
C07C 17/278 (2006.01)

(52) U.S. Cl.
CPC ........... G01N 1/4044 (2013.01); C07C 19/10 (2013.01); G01N 21/3577 (2013.01); G01N 33/2835 (2013.01); C07C 17/278 (2013.01); C07C 17/281 (2013.01); C07C 21/18 (2013.01)

(58) Field of Classification Search
None
See application file for complete search history.

(56) References Cited

FOREIGN PATENT DOCUMENTS

JP 2006145498 A 6/2006

OTHER PUBLICATIONS

DelRaso, N. J. et al. "Comparative Hepatotoxicity of Two Polychlorotrifluoroethylenes (3.1 Oils) and Two Chlorotrifluoroethylene (CTFE) Oligomers in Male Fischer 344 Rats" Fundamental and Applied Toxicology 17, 550-562 (1991) (Year: 1991).*
Kinkead, E.R. et al., "Subchronic Studies of Chlorotrifluoroethylene," Harry G. Armstrong Aerospace Medical Research Laboratory Human Systems Division, Jun. 1989, 72 pages.
"SDS—Safety Data Sheet," Halocarbon Products Corporation, 6 pages.
Kutzman, R. et al., "1989 Toxic Hazards Research Unit Annual Report," NSI Technology Services Corporation—Environmental Sciences, Oct. 1990, 19 pages.
Kutzman, R et al., Genotoxicity Assessment of Mixed Oligomers of Chlorotrifluoroethylene Using a Battery of in Vitro and in Vivo/in Vitro Assays, NSI Technology Services Corporation, Nov. 1, 1990, 90 pages.
Brashear, WT et al., "Storage Stability of Pctfe Carboxylic Acid Metabolites," Mantech Environmental Technology, Inc. Oct. 1, 1992, 29 pages.
Kutzman, RS et al., "1989 Toxic Hazards Research Unit Annual Report," NSI Technology Services Corporation, Oct. 1, 1990.
Kinkead, ER et al., "Subchronic Vapor Inhalation Toxicity Studies on 3.1 Oil in Male Fischer 344 Rats," Inhalation Forum for Respiratory Research, pp. 357-377, Jan. 1, 1991, 22 pages.
Kinkead, ER et al., "Subchronic Inhalation Studies on Polychlorotrifluoroethylene (3.1 Oil)," International Forum for Respiratory Research, pp. 433-451, Apr. 1, 1990, 20 pages.
Kinkead, ER et al., "Subchronic Studies of Chlorotrifluoroethylene," NSI Technology Services Corporation, Jun. 1, 1989, 72 pages.
DelRaso, NJ et al., "Evidence of Hepatic Conversion of C6 and C8 Chlorotrifluoroethylene (ctfe) Oligomers to Their Corresponding Ctfe Acids," Toxicology letters 59, pp. 41-49, Dec. 1, 1991, 9 pages.
Greene, RJ et al., "Confirmation of a Carboxylic Acid Metabolite of Polychlorotrifluoroethylene and a Method for Its Gc-ecd Analysis in Biological Matrices," Journal of Analytical Toxicology, vol. 16, pp. 28-32, Jan. 1, 1992, 5 pages.
Kinkead, ER et al., "Repeated-dose Gavage Studies on Polychlorotrifluoroethylene Acids," Toxicology and Industrial Health, vol. 7, pp. 295-307, Jul. 1, 1991, 13 pages.
Vinegar, A. et al., "Polychlorotrifluoroethylene (pctfe) Oligomer Pharmacokinetics in Fischer 344 Rats: Development of a Physiologically Based Model," Fundamental and Applied Toxicology, vol. 18, pp. 504-514, May 1, 1992, 11 pages.
DelRaso, NJ, "In Vitro Methodologies for Enhanced Toxicity Testing," Proceedings for the Conference on Toxicology: Applic.ations of Advances in Toxicology to Risk Assessment, Jan. 1993, 138 pages.
Jones, CE et al., "Effects of Short-term Oral Dosing of Polychlorotrifluoroethylene (polyctfe) on the Rhesus Monkey," Published In: Journal of Applied Toxicology, vol. 11(1), pp. 51-60, Feb. 1, 1991.
Brashear, WT et al., "Structural Determination of the Carboxylic Acid Metabolites of Polychlorotrifluoroethylene," Xenobiotica, vol. 22, No. 5, pp. 499-506, Jan. 1, 1992, 9 pages.
Godin, CS et al., "Evaluation of the Promotion Potential of Chlorotrifluoroethylene Trimer Acid in Male Sprague-Dawley Rats," Toxicology Letters, vol. 66, pp. 63-72, Jan. 1, 1993, 10 pages.
Gschweder, LJ et al., "Chlorotrifluoroethylene Oligomer Based Nonflammable Hydraulic Fluid. 1 Fluid, Additive, and Elastomer Development," Journal of Synthetic Lubrication, vol. 9, pp. 187-203, Oct. 1, 1992, 17 pages.

(Continued)

Primary Examiner — Medhanit W Bahta
(74) Attorney, Agent, or Firm — Alleman Hall Creasman & Tuttle LLP

(57) ABSTRACT

It is an objet to provide an oil extraction agent that is used in an oil concentration meter, that can be manufactured at low cost, that has a high oil extraction efficiency, and whose burden on the environment is small. Trimeric or higher oligomers of chlorotrifluoroethylene are contained in the overall oil extraction agent in a range between 35% by weight or more and 100% by weight or less.

4 Claims, 5 Drawing Sheets

(56) References Cited

OTHER PUBLICATIONS

Van Brocklin, C, "Military Applications of Chlorotrifluoroethylene Oligomer Base Nonflammable Hydraulic Fluid," Journal of Fire Sciences, vol. 11, pp. 232-241, May 1, 1993, 10 pages.
Mattie, DR et al., "Ultrastructual Study of the Effect of Polyctfe on Primate Liver," Harry G Armstrong Aerospace Medical Research Lab Wright-Patterson AFB OH, Aug. 12, 1990, 4 pages.
Hasal, SJ, "A Model for the Multi-organ Metabolism and Nephrotoxicity of Chlorotrifluoroethylene," The University of Arizona, Ph.D. Dissertation, Apr. 9, 1998, 195 pages.
DelRaso, NJ et al., "Effects of Chlorotrifluoroethylene Oligomer Fatty Acids on Recombinant Gaba Receptors Expressed in Xenopus Oocytes," The Journal of Membrane Biology, vol. 149, pp. 33-40, Jan. 1, 1996, 8 pages.

* cited by examiner

OIL EXTRACTION AGENT CONTAINING TRIMERIC OR HIGHER OLIGOMERS OF CHLOROTRIFLUOROETHYLENE

TECHNICAL FIELD

The present invention relates to an oil extraction agent that extracts oil from a test sample.

TECHNICAL BACKGROUND

Carbon tetrachloride and tetrachloroethylene and the like, which are used as oil extraction agents to extract oil contained in a test sample, are chemicals whose effects on the environment and on the human body are a cause of concern. For this reason, restrictions are imposed on the manufacturing thereof.

In contrast, dimeric or higher polymers of chlorotrifluoroethylene, which are used in the same way as the aforementioned oil extraction agents, have no restrictions imposed thereon.

In particular, as is described in Patent Document 1, because dimers of chlorotrifluoroethylene are known to be highly efficient in oil extraction, conventionally, oil extraction agents having dimers of chlorotrifluoroethylene as their principal constituent have been used.

However, because the yield of dimers obtained by polymerizing monomers of chlorotrifluoroethylene is low, the problem arises that manufacturing costs for such an oil extraction agent are expensive.

DOCUMENTS OF THE PRIOR ART

Patent Documents

Patent Document 1
Japanese Unexamined Patent Application (JP-A) No. 2006-145498

DISCLOSURE OF THE INVENTION

Problems to be Solved by the Invention

The present invention was conceived in consideration of the above-described problems, and it is an object thereof to provide an oil extraction agent whose manufacturing costs can be kept low, that is highly efficient in oil extraction, and that imposes a lighter burden on the environment than does the conventional technology.

Means for Solving the Problem

Namely, an oil extraction agent according to the present invention contains trimeric or higher oligomers of chlorotrifluoroethylene in a range between 35% by weight or more and 100% by weight or less.

If this type of oil extraction agent is used, because the yield of trimeric or higher oligomers obtained when monomers of chlorotrifluoroethylene are made to undergo a polymerization reaction is higher than the yield of dimeric oligomers, it is possible to reduce manufacturing costs of an oil extraction agent compared to the conventional technology.

In addition, by including trimeric or higher oligomers in a range between 35% by weight or more and 100% by weight or less, it is possible to improve the oil extraction efficiency even more compared to a conventional oil extraction agent.

Moreover, because trimeric or higher oligomers of chlorotrifluoroethylene are contained therein in a range between 35% by weight or more and 100% by weight or less, it is more difficult for this oil extraction agent to be diffused in the atmosphere than a conventional oil extraction agent, so that the environmental burden can be further reduced.

The effects such as those described above that are obtained from the present invention can also be achieved by using an oil extraction agent whose principal constituent is formed by trimeric or higher oligomers of chlorotrifluoroethylene, and whose viscosity at 25° C. is between 1.30 cSt or more and 3.00 cSt or less.

In the present specification, the term 'principal constituent' refers to the particular compound whose content is the highest from among the compounds used to produce the oil extraction agent. Because of this, it should also be understood that oil extraction agents whose principal constituent is formed by trimeric or higher oligomers include not only oil extraction agents in which the content of a single type of oligomer such as trimers or tetramers is the highest, but also oil extraction agents in which the total content of all trimeric or higher oligomers is higher compared to the content of monomers and dimers.

An example of a specific embodiment is an oil extraction agent in which the oligomers are trimers.

According to a method (and device) in which an oil concentration of the oil extraction agent after the oil extraction agent has been added to a test sample and has extracted oil therefrom is measured, and in which an oil extraction agent that contains trimeric or higher oligomers of chlorotrifluoroethylene in a range between 35% by weight or more and 100% by weight or less is used as the oil extraction agent, it is possible to measure the oil concentration in a test sample at low cost while reducing the environmental burden even more than via the conventional technology.

An example of a specific embodiment is a structure in which the oil concentration is measured using infrared absorption method.

The effects such as those described above that are obtained from the present invention can also be achieved by using a method of manufacturing an oil extraction agent in which chlorotrifluoroethylene is polymerized, substances impeding oil extraction are removed, and the content of trimeric or higher oligomers of chlorotrifluoroethylene is adjusted so as to be in a range between 35% by weight or more and 100% by weight or less.

Effects of the Invention

According to the present invention, it is possible to provide an oil extraction agent that is low in cost, that is highly efficient in oil extraction, that is more difficult to be diffused in the atmosphere than a conventional oil extraction agent, and whose environmental burden is small.

In addition, because it is more difficult for this oil extraction agent to be diffused in the atmosphere than it is for a conventional oil extraction agent, loss through evaporation can be eliminated, and usage costs can also be reduced.

BEST EMBODIMENTS FOR IMPLEMENTING THE INVENTION

Figure 1:
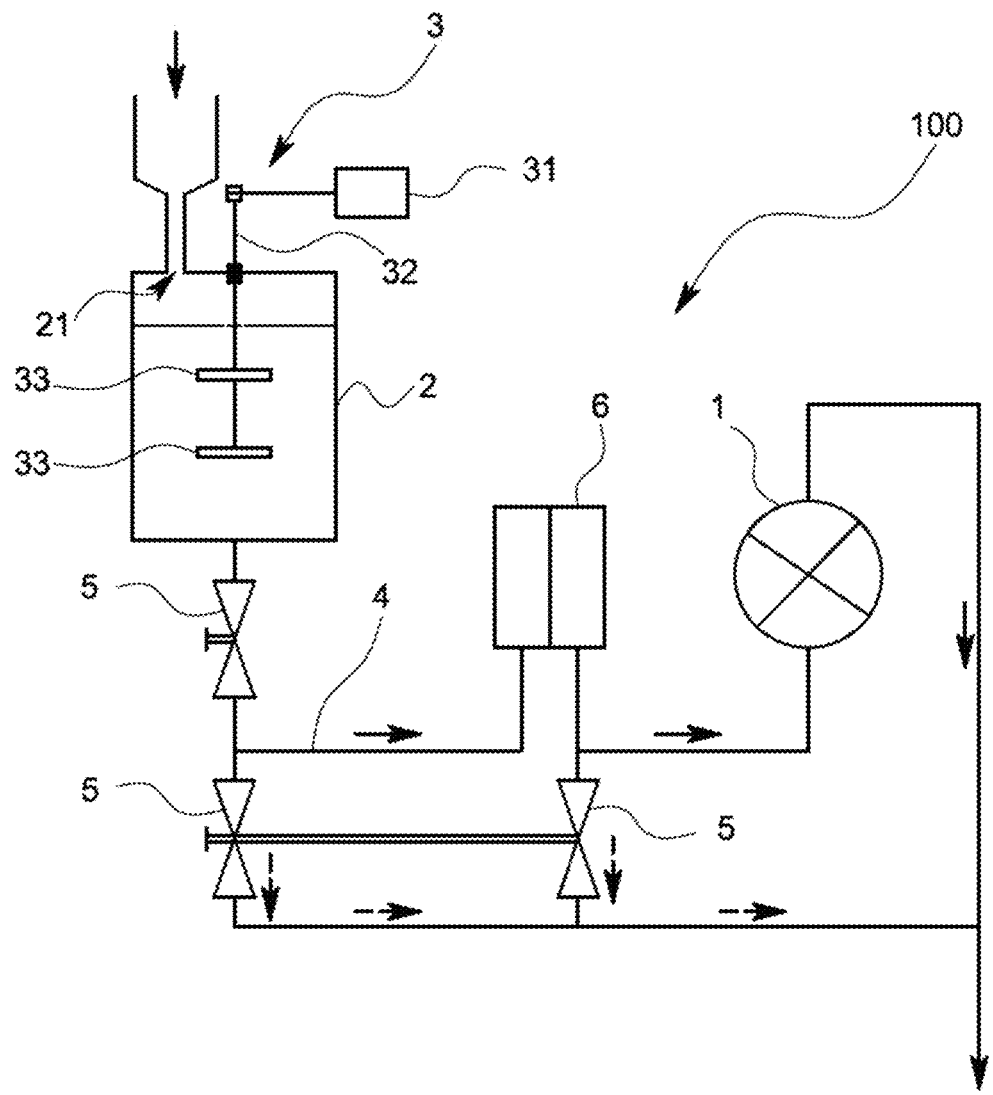
FIG. 1 is a typical view showing an oil extraction device according to an embodiment of the present invention.
Figure 2:
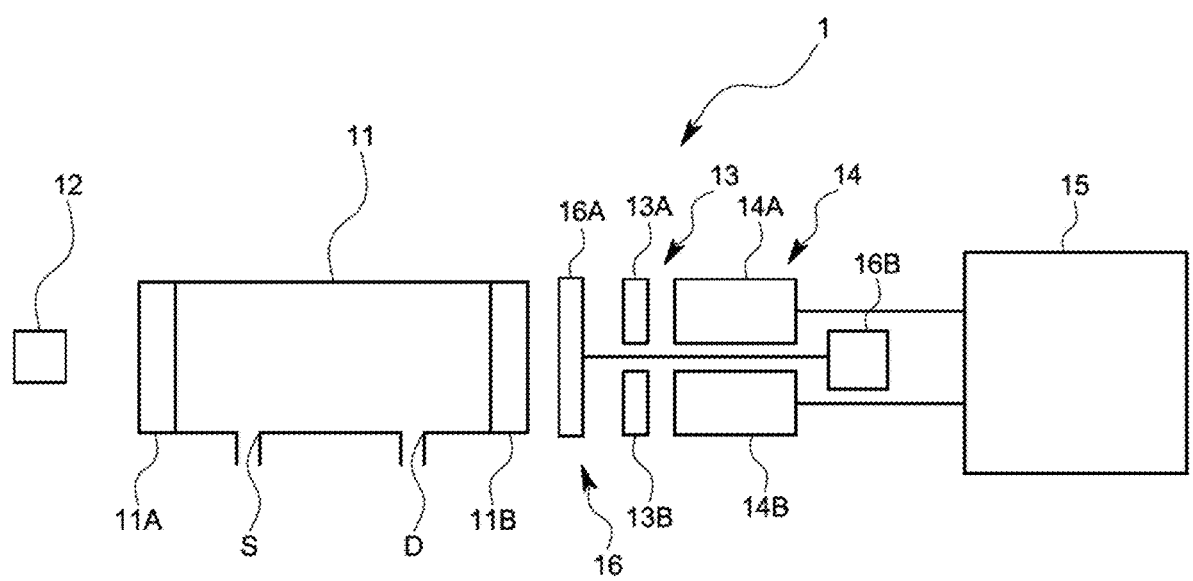
FIG. 2 is a typical view showing an oil concentration meter in the present embodiment.

Hereinafter, an embodiment of the present invention will be described with reference to the drawings.

An oil extraction agent according to the present embodiment extracts oil contained in a test sample, and is used, for example, to measure an oil concentration in a test sample of natural water, or waste water from a factory or a sewage treatment plant or the like, or of soil or the like.

The oil may be, for example, a petroleum product such as crude oil, kerosene, gasoline, or light oil or the like, or may be an animal oil, a vegetable oil, machine oil, or a hydrophobic organic solvent or the like.

The oil extraction agent contains dimers of chlorotrifluoroethylene, oligomers of chlorotrifluoroethylene, and polymers of chlorotrifluoroethylene or the like, and contains trimeric or higher oligomers of chlorotrifluoroethylene in a range between 35% by weight or more and 100% by weight or less.

The trimeric or higher oligomers may be any one from trimers, obtained by polymerizing three monomers of chlorotrifluoroethylene, to approximately icosamers, obtained by polymerizing 20 monomers of chlorotrifluoroethylene.

A method of manufacturing the oil extraction agent will now be described.

Firstly, monomers of chlorotrifluoroethylene are made to undergo a polymerization reaction while the concentration, pressure, temperature, and reaction time are controlled.

Because there is a possibility that a substance having a hydrophilic functional group which was created during the polymerization reaction will be contained in the polymerization reaction product obtained in the above-described manner, and that this substance will show surface-active action so as to impede the oil extraction, the polymerization reaction product is purified using, for example, a column which utilizes active alumina as a carrier, so that any substance having a hydrophilic functional group is removed.

The polymerization reaction product from which hydrophilic functional groups have been removed is then, for example, distilled, and the monomers of chlorotrifluoroethylene and the didecameric or higher polymers and the like, which form the reaction residue, are removed therefrom. As a result, an oil extraction agent in which the content of trimeric or higher oligomers is between 35% by weight or more and 100% by weight or less is prepared.

Next, an oil concentration measurement device 100 that measures an oil concentration in a test sample using the oil extraction agent prepared in this way will be described.

The oil concentration measurement device 100 is equipped, for example, with an extraction tank 2 that holds the oil extraction agent and a test sample so as to internally extract oil from the test sample, a stirring component 3 that stirs the oil extraction agent and the test sample held in the extraction tank 2, an oil concentration meter 1 that detects a concentration of the oil extracted by the extraction tank 2 using infrared absorption method, and a flow path 4 that connects the extraction tank 2 and the oil concentration meter 1 together.

The extraction tank 2 is, for example, a circular-cylinder shaped tank, and an intake port 21 that is used for loading oil extraction agent and test samples is formed in an upper portion thereof.

The stirring component 3 is provided, for example, with a vibrator 31 that is driven by a suitable power source, a stirring shaft 32 that is linked to the vibrator 31, and stirring blades 33 that are attached to the stirring shaft 32.

Above the flow path 4 there are provided electromagnetic valves 5 that control a flow of a liquid supplied from the extraction tank 2 to the oil concentration meter 1, and a filter 6 and the like that is used to remove foreign matter and moisture from the liquid supplied to the oil concentration meter 1.

The filter 6 may be, for example, a mesh-type filter that is formed from a material such as polytetrafluoroethylene (PTFE).

The oil concentration meter 1 is provided with a cell 11 to which the oil extraction agent is supplied after it has extracted oil, a light source 12 that is disposed on one end side of the cell 11, a filter portion 13 and detection unit 14 that are disposed on another end side of the cell 11, a calculation unit 15 that calculates an oil concentration based on output values from the detection unit 14, and a display unit (not shown in the drawings) that displays oil concentrations calculated by the calculation unit 15.

The cell 11 is formed, for example, in a circular-cylinder shape from a material having superior corrosion resistance such as stainless steel or the like, and apertures that are formed at both end portions thereof are sealed by circular-disk shaped window components 11A and 11B which are formed from an infrared-transmissive material such as, for example, quartz glass or the like.

A supply port S that is used to supply the oil extraction agent, and a discharge port D that is used to discharge the oil extraction agent are provided in an outer circumferential surface of the cell 11.

The light source 12 irradiates infrared light in an axial direction of the cell 11 onto the window component 11A of the cell 11.

The filter portion 13 is disposed on the opposite end side of the cell 11 from the end where the light source 12 is located, and is provided with a measurement optical filter 13A and a comparison optical filter 13B that are arranged side-by-side with each other so as to be perpendicular to the axial direction of the cell 11.

Both the measurement optical filter 13A and the comparison optical filter 13B are interference filters (i.e., bandpass filters) that are disposed between the cell 11 and the detection unit 14, and are formed so as to enable only infrared light whose wave number region is, for example, 2800-3100 $cm^{-1}$ to be transmitted, while blocking the transmission of infrared light from all other wave number regions.

The detection unit 14 is disposed on the opposite side of the filter portion 13 from the side on which the cell 11 is located, and is provided with a measurement detector 14A and a comparison detector 14B.

Both the measurement detector 14A and the comparison detector 14B may be, for example, pyroelectric infrared sensors. The measurement detector 14A is disposed downstream from the measurement optical filter 13A, while the comparison detector 14B is disposed downstream from the comparison optical filter 13B.

The oil concentration meter 1 is further provided with a switching mechanism 16 that switches between the aforementioned measurement detector 14A and comparison detector 14B.

The switching mechanism 16 is provided with a light chopper 16A that is disposed, for example, between the cell 11 and the filter portion 13, and with a motor 16B that drives the light chopper 16A.

When the light chopper 16A is driven by the motor 16B, the infrared light transmitted through the cell 11 is intermittently blocked at a predetermined cycle.

The calculation unit 15 calculates oil concentrations based on output values from the measurement detector 14A and the comparison detector 14B, and may be, for example, a computer that is provided with an amplifier, an A/D converter, a CPU, memory, communication ports, and a display unit and the like, and that performs the aforementioned functions by operating in accordance with a predetermined program.

A method of measuring an oil concentration in a test sample using the above-described oil extraction agent and oil concentration measurement device 100 will now be described.

Firstly, predetermined quantities of both the test sample that is to be measured and the oil extraction agent are measured out respectively.

Next, these are loaded via the intake port into the extraction tank 2, and are properly stirred by the stirring component 3 so as to be mixed together.

The mixture solution is then left to stand until it separates into a solvent layer that contains the oil, and a water layer. The solvent layer exclusively is then isolated, and is supplied via the flow path to the cell 11.

Because there is a specific absorption of C—H bonds in the oil contained in the test sample, using this characteristic, infrared light is irradiated onto the cell 11 from the light source 12, and the infrared light transmitted through the cell 11 is then detected by the measurement detector 14A and the comparison detector 14B.

Based on output values from the measurement detector 14A and the comparison detector 14B which are obtained in this way, the calculation unit 15 then calculates the oil concentration, and outputs it, for example, to a display unit provided in the oil concentration measurement device 1.

According to the oil extraction agent formed in the above-described manner, and to the oil concentration measurement method or oil concentration measurement device 1 that use this oil extraction agent, the following effects can be demonstrated.

Because the yield of trimeric or higher oligomers of chlorotrifluoroethylene obtained when monomers of chlorotrifluoroethylene are made to undergo a polymerization reaction is greater than the yield of dimeric oligomers, it is possible to reduce the manufacturing costs of an oil extraction agent.

More specifically, when monomers of chlorotrifluoroethylene are made to undergo a polymerization reaction, while the dimers make up approximately 20% of the yield, the remaining approximately 80% is made up of trimeric or higher oligomers.

Because of this, compared with when a conventional oil extraction agent whose principal constituent is formed by dimers of chlorotrifluoroethylene is manufactured, the task of increasing the content of trimeric or higher oligomers via distillation or the like can be considerably curtailed.

In addition, the fraction of trimeric or higher oligomers of chlorotrifluoroethylene that was discarded when a conventional oil extraction agent was manufactured is now able to be reused, so that there is no wastage of chemicals and the burden on the environment can be alleviated.

The vapor pressure in dimers of chlorotrifluoroethylene is low, however, because the vapor pressure is even lower in the fraction of trimeric or higher oligomers of chlorotrifluoroethylene than in dimers of chlorotrifluoroethylene, it is possible to reduce atmospheric diffusion even further when the present oil extraction agent is being used, so that the burden on the environment can be reduced even further.

Because any substance having a hydrophilic functional group is removed using a column which utilizes active alumina as a carrier, any substances showing surface-active action or the like that were created as a by-product when the monomers of chlorotrifluoroethylene were made to undergo a polymerization reaction can be removed.

As a result of this, when extracting oil from a test sample, it is possible to efficiently separate the aqueous fraction from the oil extraction agent layer in the test sample that contains the oil.

Although the efficiency of conventional oil extraction using dimers of chlorotrifluoroethylene was sufficiently high, by using an oil extraction agent containing trimeric or higher oligomers in a range between 35% by weight or more and 100% by weight or less, it is possible to improve the oil extraction efficiency to an even greater degree. This fact is a significant achievement in the current climate in which it is difficult for new oil extraction agents to be developed due to the restrictions placed on the use of chemicals.

Moreover, because absorbance in a C—H bond specific absorption band (for example, 2941 $cm^{-1}$, in other words, in the vicinity of 3.4 μm) is equally low in both an oil extraction agent containing trimeric or higher oligomers of chlorotrifluoroethylene in a range between 35% by weight or more and 100% by weight or less, and a conventional oil extraction agent whose principal constituent is formed by dimers of chlorotrifluoroethylene, it is possible to accurately measure the oil concentration using infrared absorption method.

Because manufacturing restrictions and usage restrictions and the like do not apply in the case of dimeric or higher polymers of chlorotrifluoroethylene as of December, 2017, they can be used without any problem.

Because a mesh-type filer is used for the filter 6, even if an oil extraction agent whose principal constituent is formed by trimeric or higher oligomers of chlorotrifluoroethylene, and which has a higher viscosity than a conventional oil extraction agent is used, it is difficult for the filter 6 to become clogged.

The present invention is not limited to the above-described embodiment.

For example, it is preferable that, of the trimeric or higher oligomers of chlorotrifluoroethylene contained in the oil extraction agent, oligomers ranging from trimeric or higher to decameric or lower are contained in the oil extraction agent in a range between 35% by weight or more and 100% by weight or less, and more preferable that oligomers ranging from trimeric or higher to pentameric or lower are contained in the oil extraction agent in a range between 35% by weight or more and 100% by weight or less.

In addition, the content rate of the trimeric or higher oligomers is not limited to the above-described range, and may also be ranges such as the following. For example, from 35.00% by weight or more and 51.25% by weight or less, from 35.00% by weight or more and 67.50% by weight or less, from 35.00% by weight or more and 83.75% by weight or less, from 51.25% by weight or more and 67.50% by weight or less, from 51.25% by weight or more and 83.75% by weight or less, from 51.25% by weight or more and 100.00% by weight or less, from 67.50% by weight or more and 83.75% by weight or less, from 67.50% by weight or more and 100.00% by weight or less, and from 83.75% by weight or more and 100.00% by weight or less.

The content of trimeric or higher oligomers of chlorotrifluoroethylene is not limited to the above-described range, and the same types of effects as those described above can also be demonstrated by using an oil extraction agent that contains trimeric or higher oligomers of chlorotrifluoroethylene as the principal constituent thereof, and whose viscosity at 25° C. between 1.300 cSt or more and 3.00 cSt or less, and, more preferably, is between 1.40 cSt or more and 2.800 cSt or less.

If trimeric or higher oligomers of chlorotrifluoroethylene are used, viscosity is higher compared to when dimeric oligomers are used. In particular, as is described in the present embodiment, in a flow path type of oil concentration measurement device in which an oil extraction agent that has been used to extract oil is supplied via a flow path to a cell, if the viscosity of the oil extraction agent is too high, there is a possibility that the response will be delayed.

Because of this, if trimers of chlorotrifluoroethylene are contained in the oil extraction agent to 65% or more thereof by weight, then this is preferable as it enables a response to be made rapidly even in a flow path type of oil concentration measurement device such as that described above.

In the above-described embodiment, a method and device are introduced that measure an oil concentration by using infrared light, however, the present invention is not limited to this, and it is also possible for oil to be measured by using a gravimetric method or a microbalance method instead.

The method used to remove the aforementioned substances having a hydrophilic functional group is not limited to being a method in which a column that uses active alumina as a carrier is employed, and it is also possible to instead use a method in which impurities are removed by admixing water and a saturated sodium chloride solution so as to dissolve water soluble impurities, and obtain a salting out effect, or to perform filtration using active alumina and silica gel, or to perform distillation or the like.

Moreover, the oil extraction agent is not limited to being used to measure the oil concentration contained in a test sample, and may instead be used, for example, in cleaning processes and the like that remove oil from components and pipes and the like which are used in a variety of apparatuses.

In the above-described embodiment, a structure is employed in which the oil concentration measurement device 100 is provided with the extraction tank 2 and the like, however, it is sufficient if the oil concentration measurement device 100 is provided, for example, with the oil concentration meter 1 and, depending on the usage environment and on the type of test sample, such as when oil is extracted from a test sample other than a liquid, it is also possible for either all of or a portion of the structural elements other than the oil concentration meter 1 to be removed, or for other structural elements to be added thereto.

For example, instead of the oil concentration measurement device 100 being provided with the extraction tank 2, it is also possible to load the oil extraction agent and the test sample in a separately prepared container such as a separation funnel or a sealable jar, and for the oil extraction agent and the test sample to then be shaken together using a shaker, so as to extract oil in the test sample. Alternatively, it is also possible for the oil in a test sample to be extracted via a method in which a container such as a separation funnel or the like is manually shaken without a shaker or the like being used.

In cases such as these, instead of using the filter, it is possible to remove foreign matter and moisture using mesh filter paper formed from a material such as polytetrafluoroethylene (PTFE).

The method used to supply the oil extraction agent after this has extracted oil to the cell 11 may be a method in which the oil extraction agent is supplied via a flow path, or a method in which the oil extraction agent after this has extracted oil is injected into the cell 11.

Instead of providing the supply port S and the discharge port D formed in the cell 11 separately from each other, it is also possible for these to be formed by the same single aperture.

In addition to the above-described various types of oils, it is also possible for the oil extraction agent according to the present invention to be used to extract, for example, organic compounds having a hydrocarbon group such as benzene and amine, and compounds having non-polar molecules such as, for example, iodine, carbon tetrachloride, and tetrachloroethylene.

In addition to these, various modifications and combinations of the embodiment may also be employed insofar as they do not depart from the spirit or scope of the present invention.

EXAMPLES

Hereinafter, the oil extraction agent according to the present invention will described in more detail using examples, however, it should be noted that the present invention is not limited to these examples.

In these examples, a comparison is made between the oil extraction efficiencies of a conventional oil extraction agent and of oil extraction agents containing varying contents of trimeric or higher oligomers of chlorotrifluoroethylene.

As the conventional oil extraction agent, an oil extraction agent A containing dimers of chlorotrifluoroethylene in a range between 65% by weight or more and 75% by weight or less, and trimeric or higher oligomers of chlorotrifluoroethylene in a range between 25% by weight or more and 35% by weight or less was used.

After monomers of chlorotrifluoroethylene were made to undergo a polymeric reaction, and impurities were removed therefrom using an active alumina column, only trimers, or alternatively tetramers, of the chlorotrifluoroethylene were refined to 99.9% via distillation.

These trimers or tetramers of chlorotrifluoroethylene were then mixed with the oil extraction agent A in the rates given in Table 1 (see below). Accordingly, oil extraction agents S1 to S8 that each had varying contents of trimeric or higher oligomers of chlorotrifluoroethylene were prepared.

TABLE 1

|    | Trimers | Tetramers | Oil Extraction Agent A |
|----|---------|-----------|------------------------|
| R  | 0       | 0         | 100                    |
| S1 | 25      | 0         | 75                     |
| S2 | 50      | 0         | 50                     |
| S3 | 75      | 0         | 25                     |
| S4 | 100     | 0         | 0                      |
| S5 | 0       | 25        | 75                     |
| S6 | 0       | 50        | 50                     |

TABLE 1-continued

|    | Trimers | Tetramers | Oil Extraction Agent A |
|----|---------|-----------|------------------------|
| S7 | 0       | 75        | 25                     |
| S8 | 0       | 100       | 0                      |

The oil extraction efficiencies of each of these eight types of oil extraction agent were then measured as is described below.

The subject of the oil extraction was simulated oily water containing 100 mg/L of oil (B crude oil).

In the same way as is described in the embodiment above, oil extraction was performed on this simulated oily water in this example by stirring fixed quantities of the simulated oily water and the oil extraction agent for a mixing time of 40 seconds in the extraction tank 2 forming a part of the oil concentration measurement device 100.

Note that in order to reduce as far as possible measurement errors and errors caused by variations in operating times, R, which is formed solely by the oil extraction agent A, which is a conventional oil extraction agent, and the other samples were worked at the same time.

Figure 3:
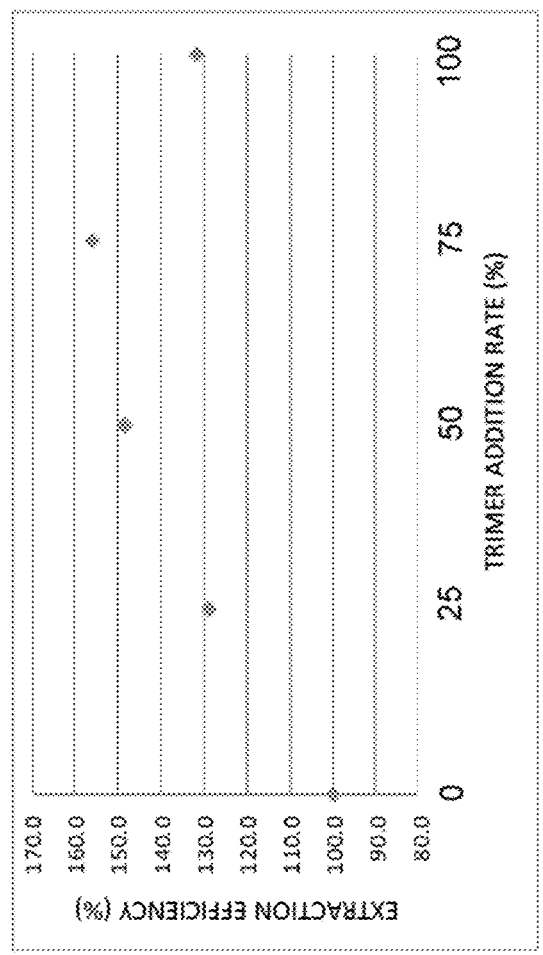
FIG. 3 shows test results obtained from an example of the present invention.
Figure 4:
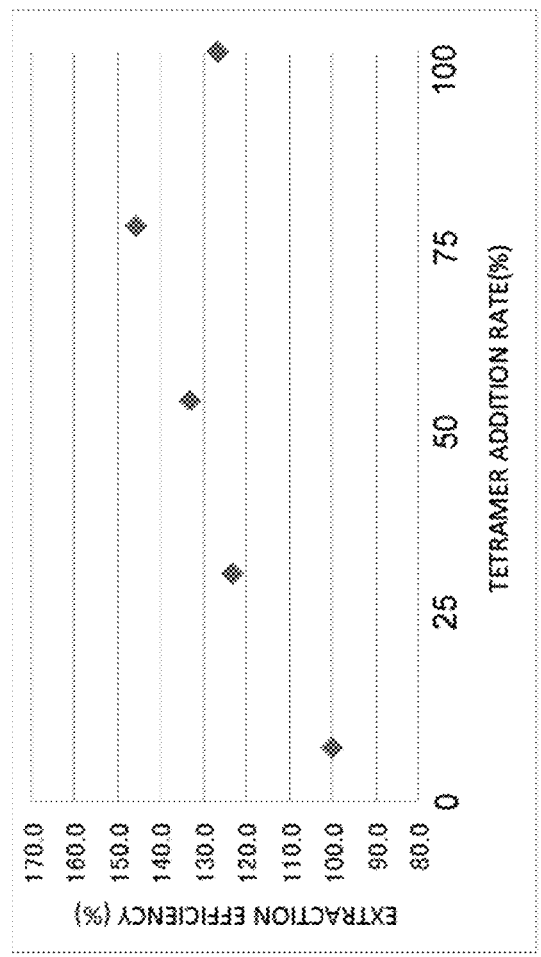
FIG. 4 shows test results obtained from the present example.

Thereafter, the oil concentrations extracted by the respective oil extraction agents were measured, and the results obtained when the degree of conformity of these oil extraction agents with the actual oil concentration of the simulated oily water was examined are shown in Table 2, Table 3, and FIG. 3 and FIG. 4.

The respective oil extraction efficiencies of S1 through S4 are shown in Table 2 (see below) and in FIG. 3 with the oil extraction efficiency of R, which is a conventional oil extraction agent, being taken as 100%.

TABLE 2

|    | Trimer Addition rate (%) | Oil Extraction Agent A Addition Rate | Oil Extraction Efficiency (%) |
|----|--------------------------|--------------------------------------|-------------------------------|
| R  | 0                        | 100                                  | 100                           |
| S1 | 25                       | 75                                   | 128.9                         |
| S2 | 50                       | 50                                   | 148.3                         |
| S3 | 75                       | 25                                   | 156.1                         |
| S4 | 100                      | 0                                    | 131.6                         |

In addition, the respective oil extraction efficiencies of S5 through S8 are shown in Table 3 (see below) and in FIG. 4 with the oil extraction efficiency of R, which is a conventional oil extraction agent, being taken as 100%.

TABLE 3

|    | Tetramer Addition Rate (%) | Oil Extraction Agent A Addition Rate | Oil Extraction Efficiency (%) |
|----|----------------------------|--------------------------------------|-------------------------------|
| R  | 0                          | 100                                  | 100                           |
| S1 | 25                         | 75                                   | 123.2                         |
| S2 | 50                         | 50                                   | 133.0                         |
| S3 | 75                         | 25                                   | 145.7                         |
| S4 | 100                        | 0                                    | 126.4                         |

From the results shown in Table 2, Table 3, FIG. 3, and FIG. 4, it can be seen that an oil extraction agent containing trimeric or higher oligomers of chlorotrifluoroethylene in a range between 35% by weight or more and 100% by weight or less enables a huge improvement to be achieved in the oil extraction efficiency compared to a conventional oil extraction agent.

Note that the present invention is not limited to the above-described trimers and tetramers, and even if pentamers or hexamers or the like of chlorotrifluoroethylene are mixed with the conventional oil extraction agent A, then if the content of trimeric or higher oligomers is set to between 35% by weight or more and 100% by weight or less, a huge improvement can still be achieved in the oil extraction efficiency compared to a conventional oil extraction agent.

It was also found that, compared with a conventional oil extraction agent, an oil extraction agent containing trimeric or higher oligomers of chlorotrifluoroethylene in a range between 67.85% by weight or more and 83.75% by weight or less showed a particularly high extraction efficiency.

In this way, it may be thought that the improvement in extraction efficiency obtained from an oil extraction agent having a higher content of trimeric or higher oligomers compared to a conventional oil extraction agent is due to the fact that oil extractability increases when a variety of molecular structures are contained in the oil extraction agent.

In addition, from the results of this example it was found that by setting the content of trimeric or tetrameric oligomers of chlorotrifluoroethylene to 65% by weight or more, a sufficiently high oil extraction efficiency could be achieved compared to a conventional oil extraction agent. Because of this, by setting the content of trimeric or tetrameric oligomers of chlorotrifluoroethylene to 65% by weight or more, even if a difference of ±10%-20% were to be generated in the oil extraction performance between each production lot, a sufficiently high oil extraction efficiency can still be maintained compared to a conventional oil concentration extraction agent that uses dimers as the principal constituent thereof.

Conventionally, it has been thought that, if the content of trimeric or higher oligomers of chlorotrifluoroethylene increases, then the content of impurities such as surfactant-type substances that are generated as a by-product of the polymerization reaction also increases.

The reason for this is that it was thought that, as the degree of polymerization increases, it becomes easier for compounds having rings and bifurcation to be generated, and also that, among these compounds, it becomes easier for substances having both a hydrophilic group and a hydrophobic group to be generated.

If the content of impurities such as those described above increases, then a layer separation delays between the test sample and the oil extraction agent, resulting in a prolonged analysis time. For example, if the content of the impurities increases to 10 mg/L or more, then 10 minutes or more are required for the layer separation.

Moreover, because these impurities are contained in the oil extraction agent, it becomes easy for moisture to penetrate the oil extraction agent. As a result, the measurement values easily become imprecise in the oil concentration measurement device using infrared adsorption method.

However, in contrast to the conventional common technical knowledge such as that described above, in the respective oil extraction agents S1 through S8 of the present example which use trimeric or higher oligomers of chlorotrifluoroethylene as their principal constituent, the content of the impurities is within a range that does not generate any problems whatsoever in the measurement of the layer separation or the infrared absorption.

It is thought that the reason for this is because the method of removing the impurities by filtration using active alumina enables the concentration of the impurities to be kept sufficiently low.

Furthermore, conventionally, it has been thought that if trimeric or higher oligomers of chlorotrifluoroethylene are used, then because there is a broad infrared absorption peak, the absorbance baseline is raised, so that an accurate measurement of the oil concentration is no longer possible.

However, in the oil extraction agents S1~S8, it was found that the infrared absorption peak was adequate for use in measuring oil concentrations. Moreover, because an oil extraction agent having a high boiling point has fewer errors in the infrared absorption, it was found that an oil extraction agent having a high content of trimeric or higher oligomers of chlorotrifluoroethylene was advantageous.

Furthermore, when the absorption of infrared light that was due to the content of trimeric or higher oligomers of chlorotrifluoroethylene in an oil extraction agent was looked at more closely, it was found that, even if the oil extraction agent contained hexameric or higher oligomers of chlorotrifluoroethylene, the infrared light absorption was adequate for use in measuring oil concentrations, and as the degree of polymerization with pentamers, tetramers, and trimers progressively decreased, the transmittance of infrared light progressively increased, so that a more distinct infrared absorption baseline could be drawn. It was found that the transmittance of infrared light varied by approximately 5% between using pentamers and using trimers.

It should be noted that an oil extraction agent that uses trimeric or higher oligomers of chlorotrifluoroethylene as a principal constituent has a tendency for the viscosity thereof to become progressively higher as the content of these trimeric or higher oligomers increases.

Figure 5:
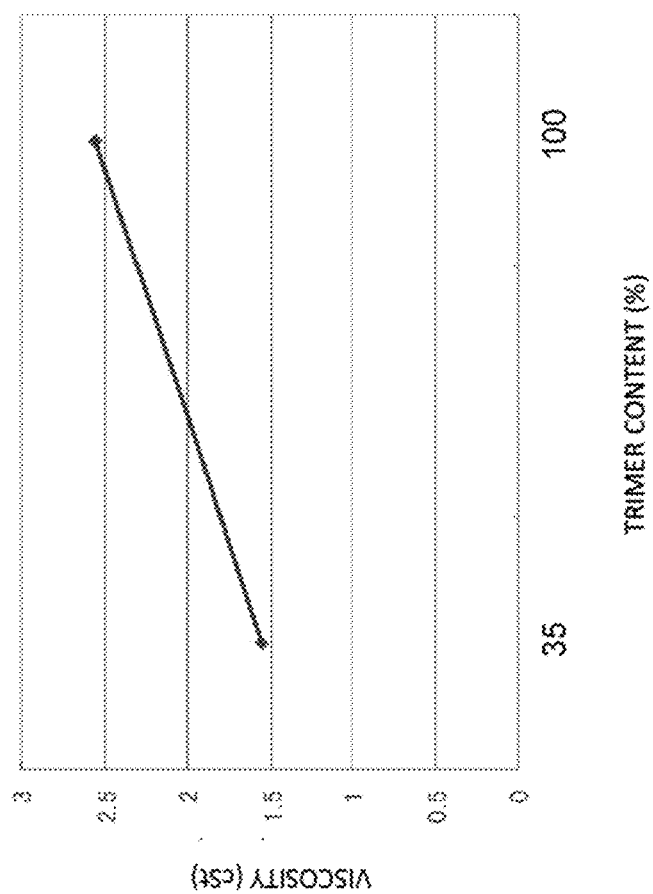
FIG. 5 shows a relationship between constituent concentration and viscosity of an oil extraction agent.

For example, as is shown in FIG. 5, it was found that there is a proportional relationship between viscosity and the content of trimers of chlorotrifluoroethylene.

According to FIG. 5, it can be seen that the viscosity at 25° C. when the content of trimers of chlorotrifluoroethylene is 35% is approximately 1.55 cSt, while the viscosity at 25° C. when the content of trimers of chlorotrifluoroethylene is 100% is approximately 2.55 cSt.

As is described above, because it can be considered that the properties of manufactured oil extraction agents vary in each production lot, if this variation is taken as being approximately +20%, then it may be thought that the viscosity of an oil extraction agent which is manufactured such that the content of trimers of chlorotrifluoroethylene is between 35% or more and 100% or less will be within a range between 1.30 cSt or more and 3.00 cSt or less at 25° C.

Because of this, in the same way as the oil extraction agents shown in Table 2 and FIG. 3, it can be thought that even an oil extraction agent that uses trimeric or higher oligomers of chlorotrifluoroethylene as the principal constituent thereof, and whose viscosity at 25° C. is within a range between 1.30 cSt or more and 3.00 cSt or less exhibits a higher oil extractability than a conventional oil extraction agent.

The results obtained when this was confirmed via experiment are shown in Table 4. Table 4 shows the results when various types of oil were extracted using two types of oil extraction agent that used trimeric or higher oligomers of chlorotrifluoroethylene as the principal constituent thereof, and whose viscosity was within the above-described range.

TABLE 4

|  | 2.6 cSt | 2.0 cSt |
| --- | --- | --- |
| B crude Oil | 23.5 | 24.0 |
| Triolein | 37.1 | 34.6 |
| Machine Oil | 62.3 | 59.2 |
| OCB | 37.2 | 47.8 |
| Light Oil | 63.4 | 63.6 |
| Vegetable Oil | 45.5 | 45.7 |
| Crude Oil A | 54.5 | 51.0 |
| Arabian Light | 22.3 | 19.8 |

In this experiment, using two types of oil extraction agent that use trimeric or higher oligomers of chlorotrifluoroethylene as the principal constituent thereof, and whose viscosity at 25° C. is approximately 2.6 cSt and approximately 2.0 cSt respectively, oil was extracted from simulated oily water via the same procedure as that described above for Table 2 and Table 3. The respective numbers in Table 4 show the oil concentrations (units: mg/L) extracted by the oil extraction agents from the simulated oily water containing the respective oils at a concentration of 100 mg/L. OCB in Table 4 represents a mixture of octane, cetane, and benzene. Note that the oil extraction agent whose viscosity at 25° C. is approximately 2.6 cSt corresponds to the oil extraction agent S4, which has a higher oil extractability than a conventional oil extraction agent, and which is shown in Table 1 and Table 2.

From the results shown in Table 4, it can be seen that an oil extraction agent containing trimeric or higher oligomers of chlorotrifluoroethylene as the principal constituent thereof, and whose viscosity at 25° C. is within a range between 1.30 cSt or more and 3.00 cSt or less exhibits a sufficiently high oil extractability with respect to various different types of oil.

Furthermore, it should be understood that the present invention is not limited to the above-described embodiment, and that various modifications and the like may be made thereto insofar as they do not depart from the spirit or scope of the present invention.

DESCRIPTION OF REFERENCE CHARACTERS

100 . . . Oil Concentration Measurement Device
1 . . . Oil Concentration Meter
11 . . . Cell
12 . . . Light Source
13 . . . Filter Unit
14 . . . Detection Unit

What is claimed is:

1. A purified oil extraction agent containing trimeric or higher oligomers of chlorotrifluoroethylene in a range between 35% by weight or more and 100% by weight or less, wherein
    surfactant impurities contained in the purified oil extraction agent are 10 mg/L or less, wherein L indicates liters of the purified oil extraction agent and mg indicates milligrams of impurities in the purified oil extraction agent,
    the purified oil extraction agent causes phase separation to occur in a period of 10 minutes or less, and
    the surfactant impurities are by-products of polymerization reactions.

2. A purified oil extraction agent whose principal constituent is formed by trimeric or higher oligomers of chlorotrifluoroethylene, and
    whose viscosity at 25° C. is between 1.30 cSt or more and 3.00 cSt or less, wherein
    surfactant impurities contained in the purified oil extraction agent are 10 mg/L or less, wherein L indicates liters of the purified oil extraction agent and mg indicates milligrams of impurities in the purified oil extraction agent, the purified oil extraction agent causes phase separation to occur in a period of 10 minutes or less, and the surfactant impurities are by-products of polymerization reactions.

3. The oil extraction agent according to claim 1, wherein the oligomers are trimers.

4. The oil extraction agent according to claim 2, wherein the oligomers are trimers.

* * * * *